United States Patent [19]

Laval et al.

[11] Patent Number: 4,958,027
[45] Date of Patent: Sep. 18, 1990

[54] 5-NITRO-2-(3,5-DIAMINO-2,4,6-TRINITROPHENYL)-1,2,4-TRIAZOLE, ITS PREPARATION PROCESS AND EXPLOSIVE MATERIAL CONTAINING IT

[75] Inventors: François Laval, Monts; Pascal Vignane, Tours, both of France

[73] Assignee: Commissariat A L'Energie Atomique, Paris, France

[21] Appl. No.: 280,555

[22] Filed: Dec. 6, 1988

[30] Foreign Application Priority Data

Dec. 8, 1987 [FR] France .................. 87 17058

[51] Int. Cl.$^5$ .................. C07D 249/14; C06B 25/00
[52] U.S. Cl. .................. 548/264.8; 149/92
[58] Field of Search .................. 548/266; 149/92

[56] References Cited

U.S. PATENT DOCUMENTS

| | | | |
|---|---|---|---|
| 2,987,520 | 6/1961 | Sickman | 260/308 |
| 3,483,211 | 12/1969 | Coburn | 260/308 |
| 3,715,398 | 2/1973 | Kaufman | 260/382 |

OTHER PUBLICATIONS

Journal of Heterocyclic Chemistry, vol. 7, No. 6, Dec. 1970, pp. 1237–1239.
Provoh, Utah, U.S.; M. A. Khan et al.: "Syntheses of N-(2,4-Dinitrophenyl)nitroazoles", p. 1237.

March Advanced Organic Chemistry, pp. 590–591 (1985).
Chem. Abstracts 99:90503n (1983).

*Primary Examiner*—Robert Gerstl
*Attorney, Agent, or Firm*—Pearne, Gordon, McCoy & Granger

[57] ABSTRACT

The invention relates to 5-nitro-2(3,5-diamino-2,4,6-trinitrophenyl)-1,2,4-triazole of formula:

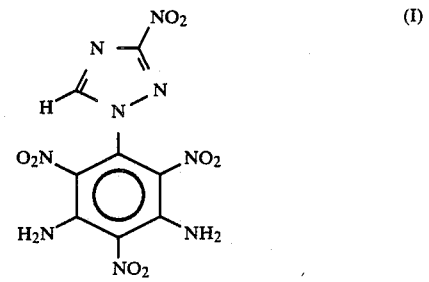

It is prepared by reacting a 1-halogeno-3,5-diamino-2,4,6-trinitrobenzene with 3-nitro-1,2,4-triazole or one of its alkali metal salts.

This triazole derivative can be used as a secondary explosive. It has a lower shock sensitivity than octogen, while still being able to supply a high energy.

2 Claims, No Drawings

5-NITRO-2-(3,5-DIAMINO-2,4,6-TRINITRO-PHENYL)-1,2,4-TRIAZOLE, ITS PREPARATION PROCESS AND EXPLOSIVE MATERIAL CONTAINING IT

DESCRIPTION

The present invention relates to a novel triazole derivative, its preparation process and its use as an explosive.

More specifically, it relates to a novel triazole derivative usable as a secondary explosive in the aerospace industry and for equipping missiles and modern armaments.

For these applications, it is of interest to use explosives having a minimum shock sensitivity, but a high power, i.e. a capacity to deliver a very high energy. It is difficult to find these two properties simultaneously in one and the same explosive. Thus, triaminotrinitrobenzene (TATB) is very insensitive to shocks, but lacks power, whereas cyclotetramethylenetetranitramine (octogen), which is very powerful, is more sensitive to shocks and attacks.

Research has recently been carried out to develop new explosives, whose shock sensitivity is similar to that of TATB, but which are still able to deliver a higher energy than the latter and which is similar to that of octogen.

The present invention specifically relates to a novel triazole derivative having these properties.

The novel triazole derivative of the invention is 5-nitro-2(3,5diamino-2,4,6-trinitrophenyl)-1,2,4-triazole in accordance with formula:

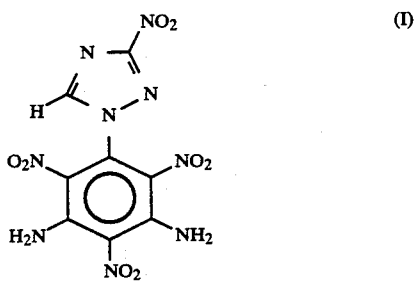

This novel triazole derivative is of interest for use as a secondary explosive, because its detonating properties are intermediate between those of TATB and octogen, with regards to the shock sensitivity and detonation velocity.

This novel triazole derivative can be prepared by a process consisting of reacting a 3,5-diamino-1-halogeno-2,4,6-trinitrobenzene of formula:

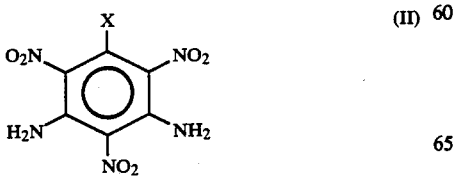

in which X represent a chlorine or fluorine atom with a 3-nitro-1,2,4-triazole of formula:

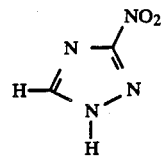

in which M represent an alkali metal or hydrogen atom.

This reaction corresponds to the following reaction diagram:

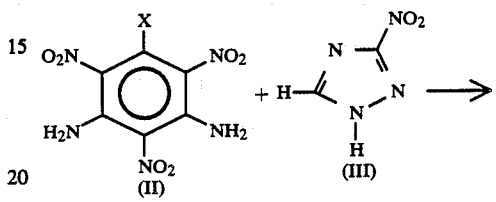

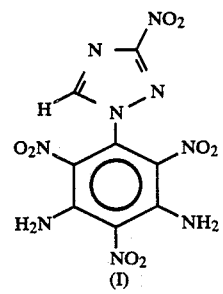

When X represents a fluorine atom, the reaction can be performed at ambient temperature, because the fluorine atom has a great reactivity with respect to nucleophilic reagents, by using the triazole of formula 111 with M representing a hydrogen atom.

However, when X represents a chlorine atom, which is less reactive, M preferably represents an alkali metal atom because it is preferable to react the 3,5-diamino-1-halogeno-2,4,6-trinitrobenzene with an alkali metal salt of 3-nitro-1,2,4-triazole. It is also preferable to carry out the reaction at a temperature above ambient temperature, e.g. 50° C. The alkali metal salt can be obtained by reacting the 3-nitro-1,2,4-triazole with an alkali metal alkoxide, in particular a lithium, sodium o: potassium alkoxide.

The starting reagents used for the preparation of said triazole derivative are commercially available products or can be obtained by conventional processes.

Thus, 3,5-diamino-1-fluoro-2,4,6-trinitrobenzene can be prepared by reacting trifluorotrinitrobenzene with a very encumbering primary amine, such as tert-butyl amine and then eliminating the tert-butyl groups by the action of trifluoroacetic acid. This synthesis corresponds to the following reaction diagram:

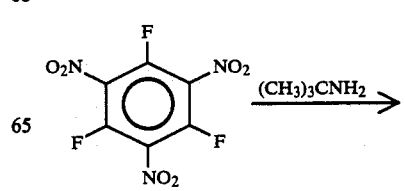

-continued

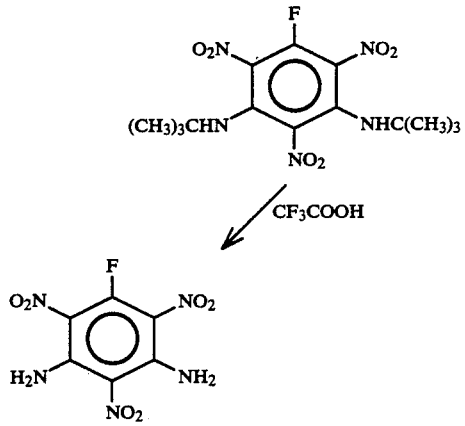

The trisubstituted (TATB) and monosubstituted impurities can easily be eliminated respectively by filtration and recrystallization.

This synthesis was in particular described by W. M. Koppes in U.S. Pat. No. 4,173,591.

3,5-diamino-1-chloro-2,4,6-trinitrobenzene can be prepared in an identical manner starting with the much more readily commercially available trichlorotrinitrobenzene. 3-nitro-1,2,4-triazole is a commercially available product. It can also be prepared from 3-amino-1,2,4-triazole using conventional methods. A widely used method consists of carrying out a diazotization by the action of nitrous acid and then a substitution of the diazonium group by the nitrite ion $NO_2^-$.

As stated hereinbefore the reaction of 3,5-diamino-1-fluoro-2,4,6-trinitrobenzene with 3-nitro-1,2,4-triazole can easily be carried out at ambient temperature.

It is advantageous to work in a water-free reaction medium using an organic solvent such as dimethyl formamide. The starting products must be dried beforehand in vacuo and the organic solvent must be dehydrated on a molecular sieve and then distilled. The reaction preferably takes place with scavenging by neutral gas, such as argon or nitrogen which has been perfectly dehydrated.

In the case where the halide used is 3,5-diamino-1-chloro-2,4,6trinitrobenzene, an alkali metal salt of 3-nitro-1,2,4-triazole is formed beforehand to facilitate the reaction, because the reactivity of the chlorine atom is too low to enable nucleophilic substitution to take place directly. In this case, the 3-nitro-1,2,4triazole is reacted with an alkali metal alkoxide ROM with M representing an alkali metal such as Li, Na or X.

The alkoxide can be obtained by the following reaction:

$$R\text{---}OH + M \rightarrow R\text{---}OM + \tfrac{1}{2}H_2$$

with R representing an alkyl radical with 1 to 3 carbon atoms.

In this case, the synthesis corresponds to the following reaction diagram:

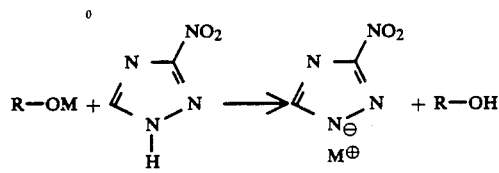

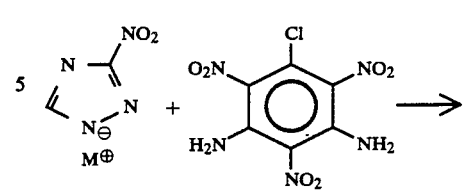

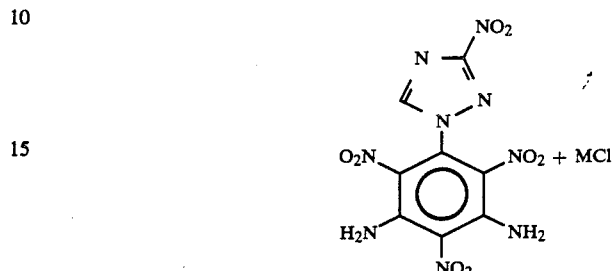

with M=Li, Na or K.

Preferably a temperature higher than ambient temperature is used, e.g. approximately 50° C.

The triazole derivative according to the invention can be used as an explosive material. In this case, the triazole derivative is generally dispersed in a thermoplastic or thermosetting binder optionally containing other additives conventionally used in such compositions (plasticizers, etc.).

Other features and advantages of the invention can be better gathered from studying the following examples given in an illustrative and non-limitative manner.

EXAMPLE 1

Preparation of 5-nitro-2(3,5-diamino-2,4,6-trinitrophenyl)-1,2,4-triazole from 1-fluoro-3,5-diamino-2,4,6-trinitrobenzene.

Synthesis of 1-fluoro-3,5-diamino-2,4,6-trinitrobenzene.

The synthesis of this fluorinated derivative takes place by reacting 1,3,5-trifluoro-2,4,6-trinitrobenzene with tert-butyl amine.

(a) Preparation of 1,3,5-trifluoro-2,4,6-trinitrobenzene.

This preparation takes place by using the synthesis method described in U.S. Pat. No. 4 173 591, whilst operating in the following way.

48 g of finely ground potassium nitrate are gradually added to a solution of 200 ml of 30% fuming sulphuric acid, whilst cooling so as not to exceed a temperature of 50° C. This is followed by the addition of 10 g of 1,3,5-trifluorobenzene and the solution is brought to 156° C. for 72 hours. After cooling to ambient temperature, the solution is extracted with 3 times 250 ml of $CH_2Cl_2$. The organic phases are then dried on $Na_2SO_4$. The organic phase is concentrated and hexane is added. Thus, a precipitate of 1,3,5trifluoro-2,4,6-trinitrobenzene is obtained with a 40 to 50% nitration yield.

(b) preparation of 1-fluoro-3,5-diamino-2,4,6-trinitrobenzene.

In a 2 liter reactor equipped with a stirring system, a thermometer, a cooling system and a nitrogen intake, introduction takes place of 5 g of trifluorotrinitrobenzene obtained in stage a) in 200 ml of $CH_2Cl_2$ dried on calcium chloride and 7.5 g of sodium bicarbonate. The reaction medium is brought to −30° C. and at this temperature is introduced into it 2.75 g of tert -butylamine (dried on potash and distilled) in 750 ml of dry the introduction taking 2 hours 30 minutes.

At the end of this operation, the reaction medium is allowed to return to ambient temperature, whilst maintaining stirring under nitrogen for 15 hours. The reaction medium is then filtered and the solvent evaporated to obtain a crude product containing 3 compounds. The crude product is then hydrolysed in a mixture of trifluoroacetic acid and dichloromethane containing 50 ml of trifluoroacetic acid and 10 ml of dichloro methane, at ambient temperature and for 20 hours. Filtration then takes place of the reaction medium and the product is extracted with 80 ml of 1,2-dichloro ethane at reflux. After concentrating the filtrate to approximately 75 ml, the product is purified by successive crystallizations. This gives 1-fluoro-3,5-diamino-2,4,6-trinitrobenzene with a yield of approximately 35% and with a melting point of 222° C.

II. Preparation of 3-nitro-1,2,4-triazole

A solution of 16.8 g (0.2 mole) of 3-amino-1,2,4-triazole in 160 ml of glacial acetic acid is added to a solution of !6 g (0.23 mole) of sodium nitrite in 70 ml of concentrated sulphuric acId at a temperature of 0 to −5° C.

After 5 minutes, there is a dropwise addition of 50 ml of water at a temperature not exceeding 0°. The solution obtained is then added to 200 ml of 10% sodium nitrite at a temperature of 45 to 50° C. This is followed by heating at 45° C. for 1 hour, acidification of the solution with 6 ml of $H_2SO_4$ to make the nitrogen oxides disappear and treatment with 12 g of urea to destroy the dissolved nitrogen oxides. The solution is then extracted with ethyl acetate. After eliminating the ethyl acetate by evaporation, the product is recrystallized in methanol and in this way 13 g of 3-nitro-1,2,4triazole are obtained. Its melting point is 210° C. and the yield is 57%.

III. Synthesis of 5-nitro-2(3,5-diamino-2,4,6-trinitrophenyl)-1,2,4triazole.

2.2 g of 3-nitro-1,2,4-triazole (0.0193 mole) obtained in the preceding stage II are dissolved in 150 ml of dimethyl formamide (DMF), dried on a screen and distilled. The solution is then agitated at ambient temperature and under nitrogen scavenging for 30 minutes.

This is followed by the addition of 5 g (0.192 mole) of 1-fluoro3,5-diamino-2,4,6-trinitrobenzene and agitation of the solution is maintained for 24 hours. The solution is then poured into one liter of cold water, accompanied by stirring.

The crude product is filtered, washed several times with water and then ether and is then dried. This gives 6.6 g of 5-nitro2(3,5-diamino-2,4,6-trinitrophenyl)-1,2,4-triazole. The yield is 95%.

Elementary analysis of the product gives the following results:

| Elementary analysis of the product gives the following results: Elementary analysis (crude product): | | | |
|---|---|---|---|
| | C | H | N |
| Found | 26.95 | 1.41 | 35.53 |
| Calculated | 27.05 | 1.42 | 35.49 |

The product is in the form of yellow crystals with a high density. The crystal density measured by the flotation method is 1.93. It decomposes without prior melting as from 260° C. It is insoluble in water and most standard organic solvents. It is soluble in dimethylformamide (DMF) and dimethyl sulphoxide (DMSO). It has the following properties:

(1) Spectroscopic properties (a) Nuclear magnetic resonance (NMR)

By adopting the following notations for the different nuclei of the molecule:

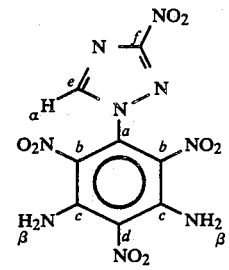

the chemical displacements with respect to the tetramethylsilane (TMS) obtained by nuclear magnetic resonance spectroscopy are as follows:

NMR of carbon $^{13}C$ at 20.15 MHz, the sample being in solution in deuterated dimethylformamide $C_f$: 162.9 ppm, $C_B$:122.8 ppm, $C_e$:249.2 ppm, $C_c$:143.3 ppm, $C_a$: 130.2 ppm, $C_d$:121.7 ppm.

NMR$^1$H at 60 MHz, the sample being in solution is dimethyl sulphoxide (DMSO).

H$\alpha$: 9.34 ppm

H$\beta$: 9.30 ppm (b) Infrared spectroscopy

Analysis by infrared spectroscopy of the 5-nitro-2(3,5-diamino2,4,6-trinitrophenyl)-1,2,4-triazole, in the form of a dispersion in KBr pellets, gives the following characteristic bands:

$NH_2$ at 3422 cm$^{-1}(\nu_{as})$; 3313 cm$^{-1}(\nu_s)$ and 1616 cm$^{-1}$ (deformation;

$NO_2$ at 1573 cm$^{-1}(\nu_{as})$; 1301 and 1281 cm$^{-1}(\nu_s)$;

CH of the triazole cycle at 3141 cm$^{-1}$.

(2) Detonating properties (a) Oxygen balance

The oxygen balance with respect to $CO_2$ and $H_2O$ is −47.30 g of $O_2$ for 100 g of explosive.

The oxygen deficiency is consequently less important than in the case of triaminotrinitrobenzene (TATB) (−55.81g/100 g) or hexanitrostilbene (−67.5 g/100 g) of formula:

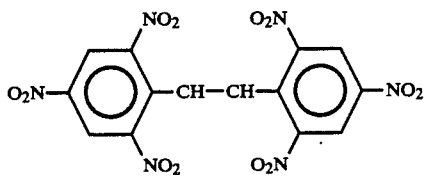

It is more important than in the case of octogen (−21.6g/100 g).

(b) Deflagration temperature.

A sample of the product (20 mg) in a stainless steel container is immersed in a bath, whose temperature is raised by 5° C./min. In the present case, the temperature at which the product deflagrates is 260° C.

(c) Thermal induction time 10 mg of product in a steel container are suddenly introduced into a bath at the measuring temperature. The time after which decomposition occurs is recorded. Taking the kinetics to be approximately zero, it is possible to calculate the activation energy. For 5-nitro-2(3,5-diamino-2,4,6-trinitrophenyl)-1,2,4-triazole, deflagration occurs after 5 seconds for a temperature of 288° C. The activation energy is 23.9 kcal/mole.

(d) Detonation velocity

The detonation velocity calculated on the basis of the formula of the compound according to the method of Rothstein and Petersen described in Propellants and Explosives, 4, pp. 56–60, 1979 is, for the crystal density, 8240 m/s.

For comparison, using the same method, the detonation velocity of TATB is 7870 m/s and that of octogen is 9050 m/s.

(e) Shock sensitivity

The shock sensitivity of 5-nitro-2(3,5-diamino-2,4,6-trinitrophenyl)1,2,4-triazole was determined with the aid of a 5 kg pendulum ram, the 30 mg sample being deposited on sandpaper. The test was performed in accordance with the Bruceton method. The height H and energy $E_j$ leading to a 0.5 pyrotechnic reaction probability are:

$H_{(50)} = 51.3$ cm $E_j = 25.2$ J.

Thus, 5-nitro-2(3,5-diamino-2,4,6-trinitrophenyl)-1,2,4-triazole would appear to be an explosive with a limited shock sensitivity, intermediate between octogen ($H_{(50)} = 15$ cm) and TATB ($H_{(50)} > 72$ cm).

EXAMPLE 2

Preparation of 5-nitro-2(3,5-diamino-2,4,6-trinitrophenyl)-1,2,4-triazole from 1-chloro-3,5-diamino-2,4,6-trinitrobenzene.

I. Preparation of 1-chloro-3,5-diamino-2,4,6-trinitrobenzene.

In a 4 liter reactor equipped with a stirrer, a cooler and a thermometer are placed 1.5 liters of dichloromethane dried on $CaCl_2$, 22g (0.3 mole) of distilled tert-butyl amine and 12.6 g of finely ground sodium bicarbonate. Dropwise addition takes place of a solution of 11.7 g (0.037 mole) of trichlorotrinitrobenzene (recrystallized three times in chlorobenzene) in 400 ml of dry $CH_2Cl_2$ over a time of approximately 2 hours. The reaction mixture is refluxed for 15 hours.

After evaporating the dichloromethane, a crude product is obtained, which is hydrolysed for 20 hours at ambient temperature using a trifluoroacetic acid/dichloro methane mixture (50/10 ml).

The 1-chloro-3,5-diamino-2,4,6-trinitrobenzene is recovered by extraction with 1,2-dichloroethane at reflux, followed by successive crystallizations. The yield is 10 to 12%. The elementary analysis of the product is as follows:

|  | C | H | N |
| --- | --- | --- | --- |
| Found | 26.06 | 1.41 | 24.96 |
| Calculated | 25.96 | 1.45 | 25.23 |

II. Preparation of 5-nitro-2(3,5-diamino-2,4,6-trinitrophenyl)1,2,4-triazole.

0.8g of sodium (0.0348 mole) is added to a mixture of 50 ml of absolute ethanol and 120 ml of n-hexane (dried on sodium). Following the reaction, introduction takes place of 3.9 g of 3-nitro1,2,4-triazole (0.0342 mole) obtained in example 1 (stage II) and refluxing takes place for 30 minutes. Cooling takes place to about 30° C., followed by the addition of 9.5 g of 1-chloro-3,5-diamino2,4,6-trinitrobenzene (0.0342 mole) and it is maintained for 2 hours under stirring at 50° C. The crude product is filtered and then rinsed with cold ether.

This gives 13.5 g of the crude product 5-nitro-2(3,5-diamino-2,4,6trinitrophenyl)-1,2,4-triazole. In order to expel the sodium chloride formed, the crude product is dissolved in DMF at ambient temperature, followed by filtration to separate NaCl. The solution is then poured into 600 ml of cold water. The product is filtered, washed with ether and then dried. 8.5 g are obtained with a yield of approximately 70%.

The elementary analysis of the product gives the following results:

|  | C | H | N |
| --- | --- | --- | --- |
| Found | 27.02 | 1.33 | 35.10 |
| Calculated | 27.05 | 1.42 | 35.49 |

This product has identical physical, spectroscopic and detonation properties to those obtained with the product prepared according to example 1.

We claim:

1. 5-nitro-2(3,5-diamino-2,4,6-trinitrophenyl)-1,2,4-triazole in accordance with formula:

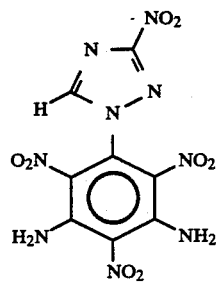
2. A composition characterized in that it comprises 5-nitro-2(3,5-diamino-2,4,6-trinitrophenyl)-1,2,4-triazole of formula:
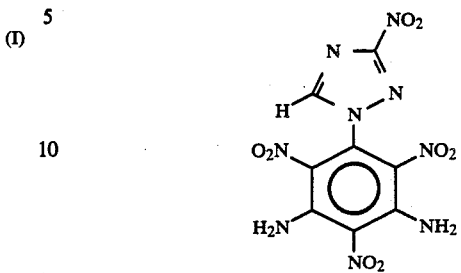
dispersed in a thermoplastic or thermosetting binder.
* * * * *